United States Patent
Cuzzani et al.

(10) Patent No.: US 7,201,720 B2
(45) Date of Patent: Apr. 10, 2007

(54) NON-CONTACTING TONOMETER

(76) Inventors: Oscar Cuzzani, 12705 Coventry Hills Way N.E., Calgary, Alberta (CA) T3K 5B1; Andrew J Barker, 71 Lynx Lane, Calgary, Alberta (CA) T3Z 1B8; Donald E. James, 4111 Brisebois Drive N.W., Calgary, Alberta (CA) T2L 2E8

(*) Notice: Subject to any disclaimer, the term of this patent is extended or adjusted under 35 U.S.C. 154(b) by 306 days.

(21) Appl. No.: 10/400,688

(22) Filed: Mar. 28, 2003

(65) Prior Publication Data

US 2003/0187342 A1    Oct. 2, 2003

(51) Int. Cl.
*A61B 3/16* (2006.01)

(52) U.S. Cl. ...................................... 600/399

(58) Field of Classification Search ......... 600/398–406
See application file for complete search history.

(56) References Cited

U.S. PATENT DOCUMENTS

| | | |
|---|---|---|
| 2,519,681 A | 4/1950 | Mages |
| 3,049,001 A | 8/1962 | Mackay et al. |
| 3,070,087 A | 12/1962 | Sittel |
| 3,181,351 A | 5/1965 | Stauffer |
| 3,192,765 A | 7/1965 | Keiper |
| 4,646,754 A | 3/1987 | Seale |
| RE34,663 E | 7/1994 | Seale |
| 5,565,939 A * | 10/1996 | Fujieda .................. 351/212 |
| 6,053,867 A * | 4/2000 | Iijima ..................... 600/399 |
| 6,288,784 B1 | 9/2001 | Hitzenberger et al. |
| 6,423,001 B1 * | 7/2002 | Abreu .................... 600/405 |
| 6,673,014 B2 * | 1/2004 | Badehi et al. .......... 600/398 |
| 2002/0173711 A1 * | 11/2002 | Walton ................... 600/398 |

OTHER PUBLICATIONS

Roos, P.A. et. al. "Laser vibrometer based on optical-feeedback-induced frequency modulation of a single mode laser diode"□□Applied Optics, Dec. 1996. vol. 35, No. 34.*

Valera, J. D. et. al. "Combined fibre optic laser velocimeter and electronic speckle pattern interferometer with a common reference beam."□□Measurement Science and Technology, 1993. vol. 4, pp. 578-582.* www.photonics.com/Spectra/NewProds/oct99/tDOPPLER.html, Mar. 19, 2002, 2 pages.

www.imageautomatioan.com/ometron/faq.html, Mar. 25, 2002, 10 pages.

OMETRON VH300+ technical specifications, 1 page.

OMETRON VS100/VS1000 Single-Point Laser Doppler Vibrometer technical literature, 4 pages.

(Continued)

*Primary Examiner*—Max F. Hindenburg
*Assistant Examiner*—Fangemonique Smith
(74) *Attorney, Agent, or Firm*—Sean W. Goodwin; Linda M. Thompson

(57) ABSTRACT

Apparatus and method for measuring Internal Ocular Pressure (IOP) comprises applying a perturbing vibration into an eye over a range of frequencies. A vibrational response of the surface of the eye is measured such as by using a laser velocimeter, the vibrational response including velocity and rate of change of the phase lag. Further, geometric properties such as volume of the eye are measured such as by using a laser interferometer to measure characteristics such as the eye's axial length and cornea thickness. Use of multiple characteristics normalizes the effect of an eye's mechanical and geometric properties and thereby more accurately determines the IOP.

18 Claims, 5 Drawing Sheets

OTHER PUBLICATIONS www.findarticles.com/cf_dls/g2601/0005/2601000595/p1article_ihtml, Mar. 19, 2002, 2 pages.

www.ascrs.org/publications/jcrs/lsmay00.htm, Mar. 19, 2002, 2 pages.

www.venus.co.uk/iga/SimpFact/sf096.htm, Mar. 19, 2002, 2 pages.

http://willsglaucoma.org/terminology.html, Mar. 19, 2002, 3 pages.

www.cdi.pub.ro/CDI/Medical/disc7/sld017.htm, Mar. 19, 2002, 1 page.

http://research.opt.indiana.edu/Libraray/InterferometricMeas/InterferometricMeas.html, Mar. 18, 2002, 16 pages.

www.usa.canon.com/indtech/encoders/lv20z.html, Mar. 25, 2002, 1 page.

www.usa.canon.com/indtech/encoders/lv20zspec.html, Mar. 25, 2002, 1 page.

Young, W. Jr., Meyers, J., and Hoad, D., A Laser Velocimeter Flow Survey Above a Stalled Wing, 1978, 4 pages (title page, pp. 41-43), NASA Technical Paper 1266.

Meyers, J. and Murphy, R., Frequency Domain Laser Velocimeter Signal Processor, Nov. 27-28, 1990, 5 pages (title, 1, 2, 11, and 12), Technology 2000 National Aeronautics and Space Administration.

www.lerc.nasa.gov/Other_Groups/OptInstr/Idv.html, Mar. 18, 2002, 1 page.

www.mne.umassd.edu/facilities/laserlab.html, Mar. 18, 2002, 1 page.

www.spie.org/web/meetings/calls/pw98/pw98call_bo04.html, Mar. 18, 2002, 3 pages.

www.opt.indiana.edu/riley/HomePage/NonContact/TEXT_Non_Contact.html, Mar. 18, 2002, 5 pages.

www.analytic-web.com/polytec-com/1_vib/vib_uni_las.html, Mar. 20, 2003, 3 pages.

www.analytic-web.com/polytec-com/1_vib/vib_uni_vib.html, Mar. 20, 2003, 5 pages.

http://archopht.ama-assn.org/issues/v118n1/abs/ecs90061.html, Mar. 18, 2002, 2 pages.

* cited by examiner

NON-CONTACTING TONOMETER

FIELD OF THE INVENTION

The present invention relates to a non-contacting apparatus and methodology for the acquisition of physical, physiological and structural characteristics of an eyeball and more particularly for determining a measure of the internal ocular pressure of the eye. More particularly, vibration is induced in the eye and a laser velocimeter and laser interferometer are employed.

BACKGROUND OF THE INVENTION

Measuring the intraocular pressure (IOP) of an eye is a measurement of the pressure of the fluid inside the eyeball. It is advantageous to monitor IOP as it is an indicator of the health of the eye. Excessively high IOP can be associated with optic nerve damage, such as in the case of glaucoma.

An eyeball may be deemed analogous to an elastic vessel filled with a fluid of a substantially incompressible nature. One can compare such an elastic vessel to a balloon having extensible walls wherein an increase in volume in the fluid produces a change in the internal pressure balanced by an expansion of the vessel wall. Fluids inside the eye circulate in a substantially continuous fashion and an increase in the influx of fluids normally accompanies a similar increase in the outflow of fluid. In cases where the outflow does not keep up with inflow, an increase in internal pressure and an expansion of the eye will occur. In situations where the rigidity of the eye's wall is increased, two effects are observed: increases in the internal pressure are greater per increase in fluid inflow; and a smaller overall expansion of the volume of the eye.

The change in the expansion of the eye depends on the extensibility of the walls of the eyeball. The more extensible the wall, the greater the ability for eye's volume to increase in response to a fluid volume change. The less extensive is the wall, the less capable is the eyeball to cope with fluid volume change and the more the fluid pressure will increase.

Typically, in biomedicine, pressure such as IOP is not measured directly because of the invasive nature of placing a pressure sensor in the fluid of the eyeball. Therefore, determination of pressure is typically attempted using alternate less invasive methods. Consequently, while measuring intraocular pressure directly, continuously, and non-invasively is desired, it is difficult to achieve.

Moderately invasive measurements are known and have already been conducted. Devices known as "Contacting Tonometers" have been used extensively by the medical community for many years. However, their popularity and attractiveness is offset by the need to have direct mechanical contact with the eye, thus requiring an anesthetic. Further, the requirement for contact and the resulting deformation of the eye can introduce errors in the determination of IOP due to formation of tears, changes in eye volume due to compression, and as a result the variance of the physical properties of the cornea. Such prior art devices are described in U.S. Pat. Nos. 2,519,681; 3,049,001; 3,070,087; 3,192,765.

Various other attempts have been made to measure IOP discreetly or continuously by means of more indirect methods. Indirect methods have the advantage of being non-invasive, or at least less invasive than indentation and applanation tonometry. As set forth in U.S. Pat. No. 3,181,351, one such method introduces a sharp pulse of air onto the eye, while measuring the resulting deformation of the cornea. Such indirect methodology usually suffers from two limitations: lack of accuracy and a lack of absolute value in resulting measurements.

Both the invasive and indirect methods assume that all eyes have substantially equivalent physical properties. This is not the usual case. What is required is a means to determine IOP which is cognizant of the variability of characteristics from eye to eye. Some have attempted to relate IOP to an eye's mechanical response to gross stimulus and nominal eye characteristics and others have associated IOP with measures of eye geometry.

In contradistinction to the prior art, Applicants have sought to determine both characteristics specific to the structure of the eye and characteristics which vary as a result of changes in IOP.

SUMMARY OF THE INVENTION

An apparatus and method are provided that represent a new, indirect method for a discreet or continuous and non-contact measurement of IOP. IOP influences the mechanical properties of the eye and vice versa. Measuring these mechanical properties permits one to better deduce information about the IOP. The advantages of this technique include lack of contact with the eye and an associated increase in comfort while decreasing the level of training of technicians required to perform the measurement. As a result, the instrument may also be applied at point-of-care. Further, by removing the prior art reliance upon assumptions regarding nominal eye characteristics, the results are more accurate over a wider range of population.

Applicant's obtain certain measurements including establishing fundamental mechanical eye characteristics which are unique to each specific eye, and which can mask the factors which identify variations in IOP. Further, additional geometric measurements are obtained which, when combined with the eye's mechanical characteristics, enable more accurate determination of IOP despite variations from eye to eye.

A methodology and apparatus are provided which, in a preferred embodiment, measures characteristics or the physical properties of the eye as a whole, including at least the tensile properties and the corneal properties, in particular, based on its vibrational characteristics, including but not limited to resonant vibrations and harmonics. The vibrational characteristics are preferably induced using an acoustical, non-contacting source.

In accordance with one embodiment of the present invention, a tonometer instrument is provided which does not require contact with the eye and which corrects or normalizes for the variations in physical properties of the eye. When an acoustical energy is applied to the eyeball, the velocity of the corresponding vibrational oscillations or response of the eye is measured and physical information of the eye may be deduced. The vibrational response is measured over a range of frequencies. In a preferred embodiment, it is noted that as the frequency of the exciting or perturbing oscillations pass through a harmonic of the eye, the velocity will reach a peak. The appearance of the peak can shift in frequency and in magnitude as the IOP varies. Further, the phase shift or lag, between the perturbing vibration and the induced vibrations of the eye is also observed to vary with IOP. Also the rate of change of phase lag with frequency is indicative of properties of the eye. By measuring one or more resonant frequencies, more physical information of the eye may be deduced.

For further normalizing the vibrational response, and contiguous with the velocity measurement, a laser interferometer is used to measure the geometry of the eye including an axial length of the eye from which the volume of the eye is deduced. Also the cornea thickness can be measured, from which additional mechanical properties such as the elasticity are deduced.

These measurements are more accurate than are possible by merely measuring the changes occurring in the corneal curvature or the force or time required to indent or flatten it. The reason for this is that when acoustic energy is used, it does not change the volume of the eye and thus does not substantially affect the pressure.

The IOP is measured by measuring vibrational properties of the cornea or eye as a whole. Characteristics which are identifiable and responsive to changes in IOP for normalizing or removing the effect of each eye's own physical characteristics include: the physical three-dimensional response to the exciting vibration, the phase lag of the response with respect to the exciting force and the amplitude and/or shape of the phase response.

The novel instrument is sensitive to two forces, that due to the IOP and that due to the tensile tension of the corneal and other eye tissue.

In a broad aspect of the invention, a method is provided for determining measures of intraocular pressure in an eye without direct contact with the eye, comprising: applying a perturbing vibration to at least a portion of the eye for inducing an induced vibration in the surface of the eye; varying the frequency of the perturbing vibration; measuring a vibrational response of the induced vibration as the frequency of the perturbing vibration is varied for establishing characteristics indicative of mechanical properties of at least the portion of the eye including at least a stiffness property of the eye; and determining measurements indicative of the intraocular pressure in the eye from the vibrational response of the eye.

More preferably, the method further comprises measuring the velocity of the vibration in the eye for establishing characteristics indicative of at least the stiffness of the eye. Preferably, acoustical energy is applied so as to induce the vibration in the eye.

More preferably, the method further comprises the steps of providing a laser velocimeter which produces signal and reference laser beams; reflecting at least the signal laser beam from the vibrating eye; and combining the reflecting signal laser beam with the reference beam for creating interference indicative of the one or more dimensional vibrational responses or motion of the vibrating eye. The measured vibration response is preferably one of determining the velocity response of the vibrating eye, or determining the phase and phase lag response of the vibrating eye.

In applying the properties determined above, the method further comprises the step of determining the vibration response of the vibrating eye as a function of the axial length of the eye which can be related to the eye's volume, and the mechanical properties of the eye. Additionally, an elastic modulus of the vibrating eye is determined as a function of the thickness of the cornea and the water content of the cornea. Accordingly, most preferably, the IOP is determined as a function of the vibrational response, the mechanical properties and the geometry of the eye.

More preferably, the method further comprising the steps of: providing a laser interferometer for producing a measuring beam and interference patterns from a plurality of beams reflected back to the interferometer; and determining the path length between at least two of the reflected beams for establishing an axial length of the eye as a geometric characteristic of the eye. One can apply the axial length of the eye for establishing characteristics indicative of at least the volume of the eye. More particularly, the method comprises determining path lengths between at least two of the reflected beams for establishing a corneal thickness as a geometric characteristic of the eye.

The method is understood to be accomplished with a variety of apparatus, some components of which are known to those skilled in the art. Namely, in a broad aspect of the invention, a non-contacting tonometer is provided comprising: means for vibrating the eye, preferably using acoustic energy; means for measuring the vibrational response from the surface of the eye, preferably using a laser velocimeter; and means to calculate mechanical properties of the eye including at least its volume, preferably using a laser interferometer. A laser interferometer is preferably employed to measure the axial length of the eye and more preferably also to measure the thickness of the cornea to improve the accuracy of the IOP determination.

DETAILED DESCRIPTION OF THE PREFERRED EMBODIMENT

Figure 1:
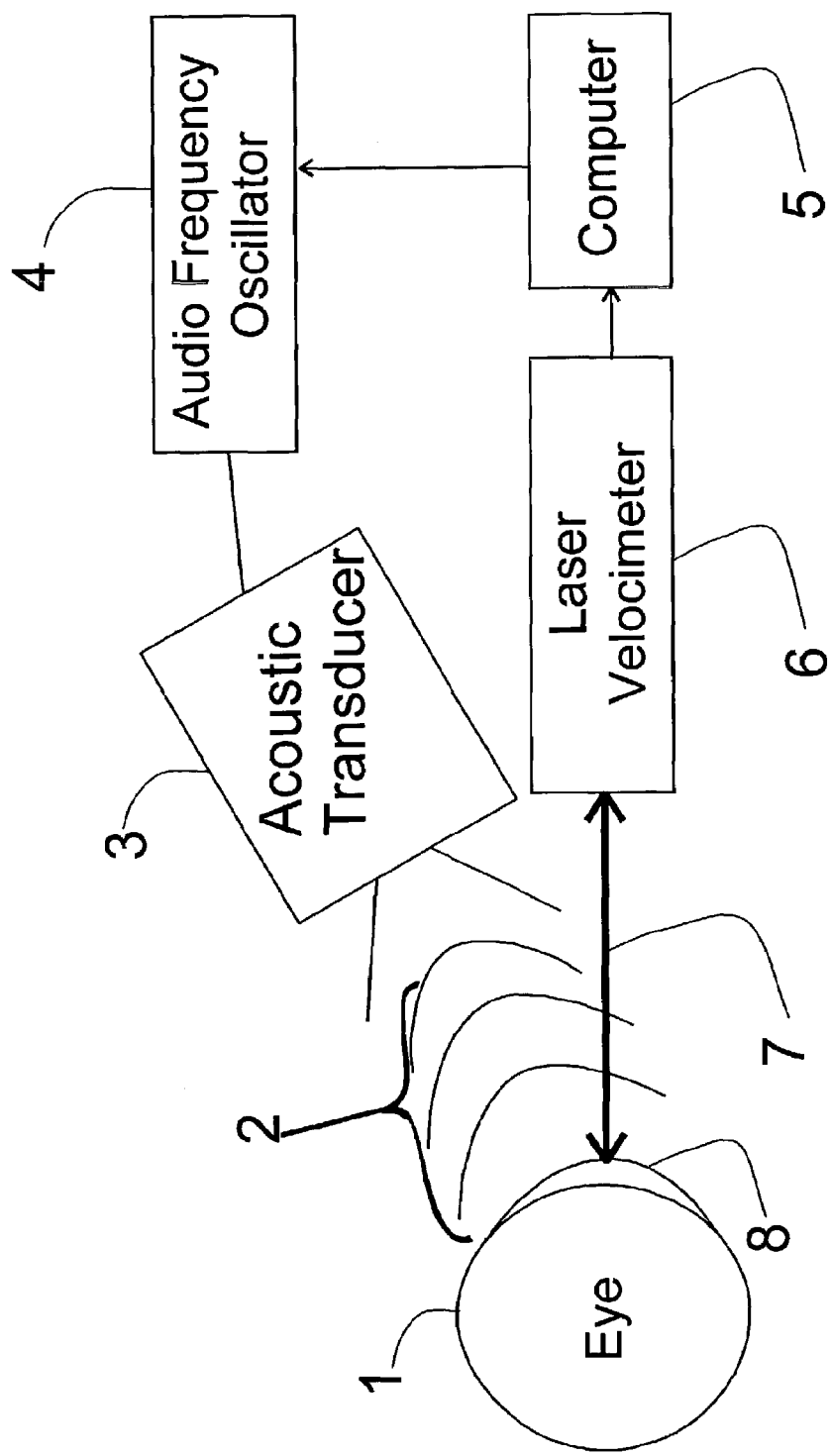
FIG. 1 is a block diagram of an acoustic transducer exciting an eye while a laser velocimeter measures vibrational response such as movement of oscillations of the eye.

Have reference generally to FIG. 1, the importance of measuring the mechanical properties (such as compliance, elastic properties or stiffness) of the eye 1, and more specifically of the cornea, stems from the fact that the variability of the elastic modulus between eyes is associated with variations in the apparent IOP as derived using other direct and indirect measurements. Considering that the eye 1 is a near-sphere, the volume for a normal emmetropic eye with an axial length of 24 mm is about 7238 microliters. As a baseline, and based on measurements of the change in volume and pressure in such a nominal eye, a change in eye volume of about 80 microliters results in about a 50-mm Hg change in IOP (from 10 to 60 mm of Hg). Typically, within the normal range of the human eye, volume changes occur between about 10 to 40 mm Hg, and are less beyond about 40 mm Hg.

Applicant's have found that the IOP pressure in the eye 1 affects its vibrational response to a stimulus. The eye can be stimulated by driving the eye with acoustic excitation. One way to determine the response of the eye 1 to such acoustic excitation is through the use of a laser velocimeter 6 and the techniques of Laser Doppler Vibrometry (LDV). A device such as one similar to an Ometron VS 100 from Image Automation Ltd., can accurately measure the velocity of vibration of the outer wall of the eye 1 or the cornea 8 when perturbed by a sonic wave. Typical specifications include vibration frequency: <0.01 Hz to over 300 kHz and vibration velocity measurement of +/−0.001 to 1000 mm/s (40 micro ips to 40 ips) peak.

A coherent signal laser beam 7 (such as a 1 mW helium-Neon class II laser) is projected onto the cornea 8. Preferably the signal beam 7 comprises long A coherent signal laser beam 7 (such as a 1 mW helium-Neon class II laser) is projected onto the cornea 8. Preferably the signal beam 7 comprises long coherent light over a narrow spectrum. The signal beam 7 strikes the vibrating surface of the cornea 8 and is reflected back into the laser velocimeter 6 where it is recombined with a reference beam. Light scattered back from the surface is shifted in frequency by an amount proportional to the velocity of the vibration of the surface. This is the Doppler effect. Interference between signal 7 and reference beams generates signals from which the Doppler shift and the velocity of the vibrating surface is derived. The frequency shift is measured to produce an instantaneous velocity signal which can be analyzed. Suitable lasers used in the velocimeter include the Ometron HeNe and Nichia laser diodes available from Nichia America Corporation of Mountville, Pa.

There is a definite association between the vibrational response and the IOP, however the measured changes in vibrational response of the eye are very small (5–10 Hz for an IOP range of 5 to 35 inches of water, being 10–65 mm Hg). Also the amplitudes of the vibrations are very small (2–20 nm) when driven by an acoustical excitation of 1 pascal pressure. The shift of harmonic frequencies or amplitude produced by a change in the IOP is crucial for vibration analysis to detect IOP. Vibration or movement of the eye 1 in the orbit can act to mask these small vibrations induced in the eye 1 itself. Accordingly, in an optional enhancement, the measurements are improved by measuring the vibrational difference between the cornea and a reference location such as the back of eye. Basically, such masking effects can be minimized by making two simultaneous measurements from two different locations from the eye.

Figure 4:
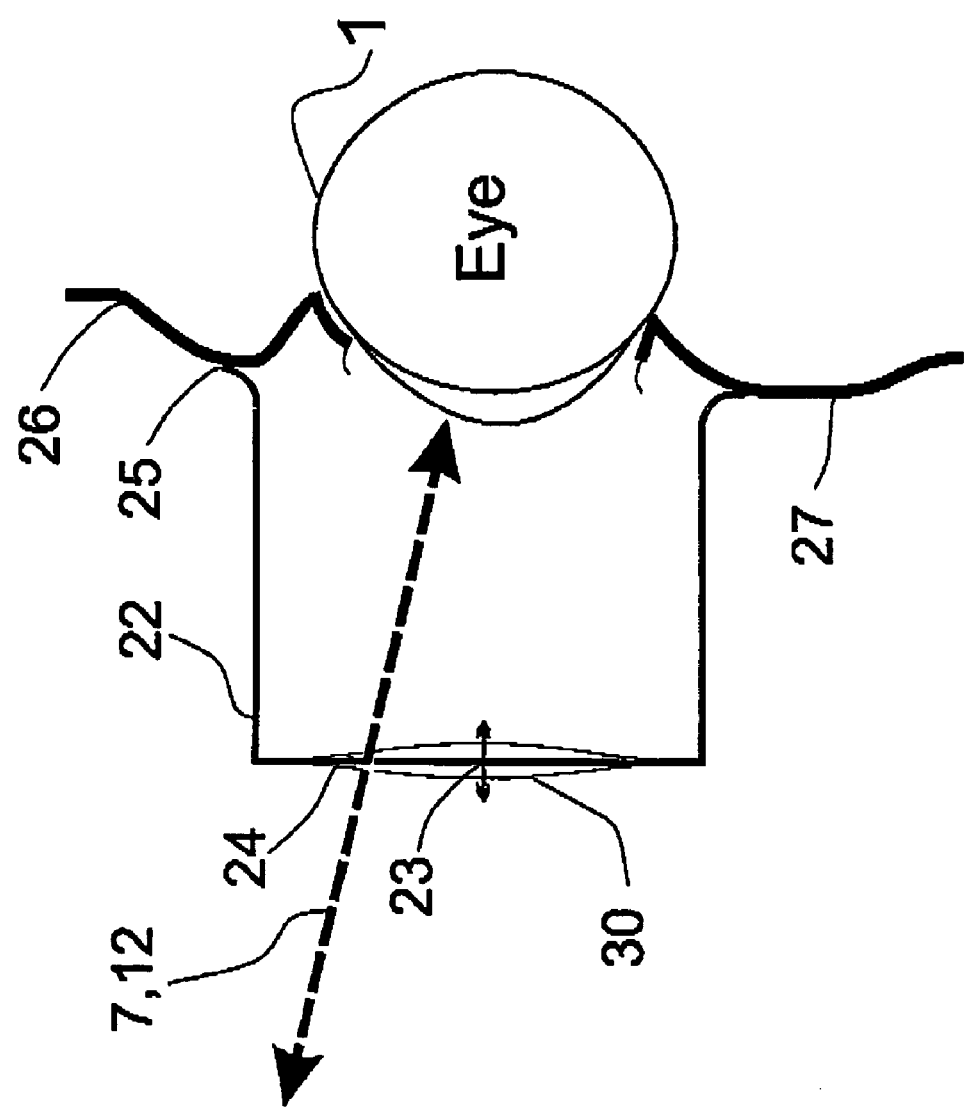
FIG. 4 is a schematic of an optional soft cup used to concentrate acoustical energy used to perturb an eye.

To deliver the necessary acoustical excitation or perturbing vibration to the eye, an acoustical wave generator such as a standard audio speaker can be used. The speaker is placed in close proximity (2–4 in) to the eye and driven at approximately 100 dB. As shown in FIG. 4, to improve the delivery of the acoustical excitation, a soft cup 22 with a driven diaphragm 30 at the closed end 23 can be used to concentrate the energy into the eye.

Each eye has a different volume and mechanical properties such as elasticity, therefore these variances must be taken into consideration when calculating IOP. To do this, laser interferometry similar to that described in U.S. Pat. No. 6,288,784 to Hitzenberger et al. is used to accurately measure the corneal thickness. The entirely of U.S. Pat. No. 6,288,784 is incorporated herein by reference. Corneal thickness is related to corneal stiffness, a major source of error in contact tonometry. Axial length of the eye is related to the eye's volume. The eye's vibrational response is normalized with the axial length and corneal thickness to yield a more accurate IOP.

While the actual normalization of the eye's characteristics may be numerically determined, it is understood that a better measure of the IOP can be determined as a function of some basic variables including:

Ro is a function of V, Ri, and k1;
E is a function of P, $H_2O$, k2; and
IOP is a function of V, E, Rik3.
Where:
Ro=is the vibrational response of the eye;
V=Eye volume (axial length);
Ri=Biomechanical rigidity of the eye;
E=Elastic modulus of the eye;
P=Thickness of the cornea;
$H_2O$=Water content of the cornea (which is substantially constant); and
k1, k2 and k3=Constants.

The determination of IOP is a multivariate analysis which is dependent upon a large body of empirical data. Practically, the resulting relationships are complex and the effects of the various parameters which affect the IOP pressure measurement have to be found empirically and preferably with the use of finite element analysis. As those of skill in the art are aware, a variety of numerical techniques can be applied to obtain the solution. One approach is to apply neural networks and statistical methods to establish these relationships and to confirm the results of finite element analysis.

In greater detail, and again with reference to FIG. 1, there is illustrated a system for exciting and measuring the resulting vibrations of an eye. An acoustic transducer 3, is driven by an audio frequency oscillator 4. Both the frequency and amplitude of said oscillator are controlled by a computer 5 which is preferably common to all elements of the instrument. The amplitude of the oscillator 4 is controlled such that the force of the acoustic wave 2 exciting the eye 1 is known. Simultaneously, the computer 5 controls and performs velocity and phase measurements via a laser velocimeter 6 reflecting a laser light beam 7 off of the eye 1 and interfering with a reference beam (not shown). The frequency of the oscillator 4 is swept across a range of interest while the computer 5 determines and records vibrational responses of the eye 1 including the resonant or harmonic frequencies under investigation.

Figure 2:
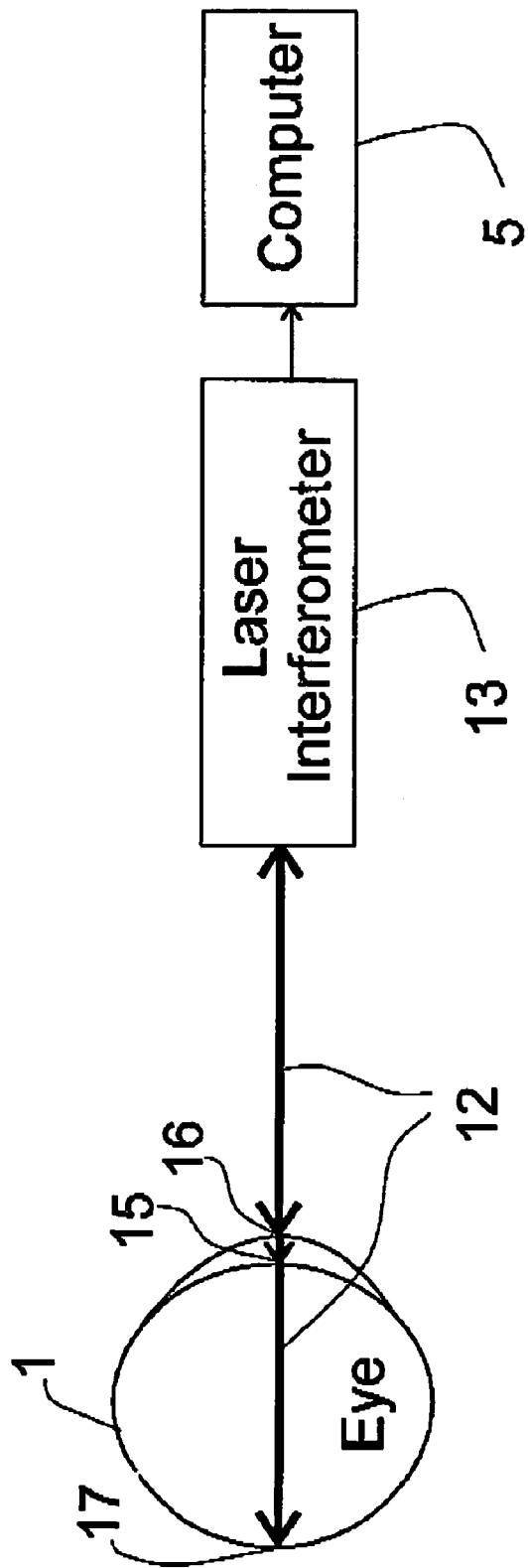
FIG. 2 is a block diagram of a laser interferometer measuring both the axial length and the cornea thickness of the eye.

Further, and referring to FIG. 2, there is illustrated a system for measuring the axial length and the corneal thickness of an eye 1. A laser light beam 12 is shone into the eye 1. The light beam 12 is reflected back to the laser interferometer 13 causing interference patterns. The reflections include light from the outer 16 and inner 15 surfaces of the cornea 8 and from the back 17 of the eye 1. The interferometer 13 measures these patterns and determines three path lengths. Conveniently, the sane microprocessor or computer 5 controls the interferometer 13, and calculates the axial length and the cornea thickness from the three path lengths.

EXAMPLE

Figure 3A:
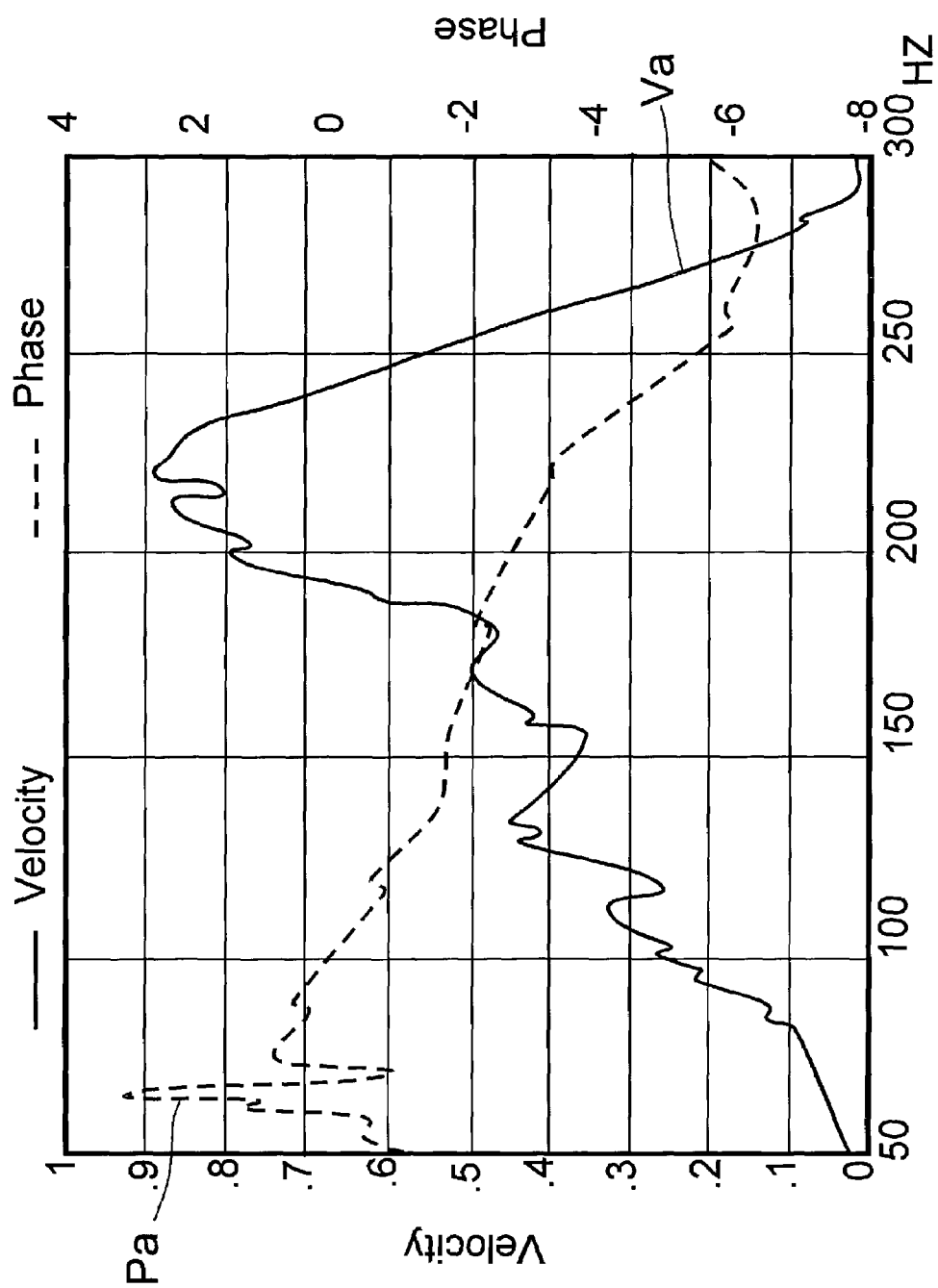
FIGS. 3a & b are plots of the vibrational response, of velocity and phase lag, in an experiment using a porcine's eye.
Figure 3B:
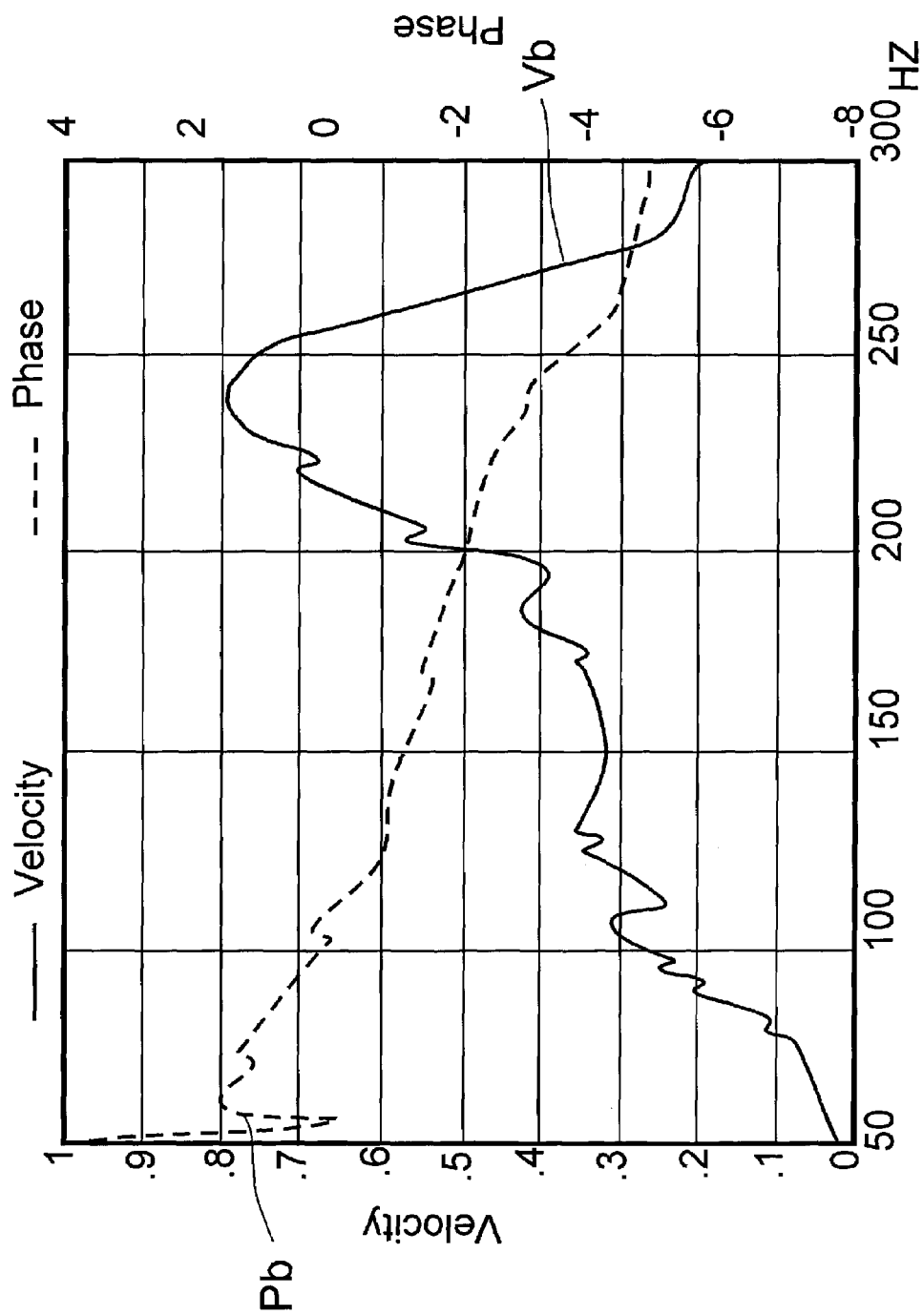

Referring to FIGS. 3a and 3b there are illustrated velocity, phase lag and one or more points of resonance measured from a porcine eye at low and high IOP respectively. In this example, a measured pressure, representing IOP, was applied to the eye with an invasive fluid connection. Acoustical energy was applied using the frequency oscillator through a range of about 50 to 300 Hz for inducing vibrations in the eye. Preferably a range of frequencies is applied so as to aid in identifying occasional points of resonance. A laser velocimeter was applied to the surface of the eye to measure the vibrational response, namely velocity, at the surface of the eye.

Referring specifically to FIG. 3a, trace Va illustrates the vibrational velocity response of the acoustically excited eye having a low IOP. Note a maximal velocity inflection in trace Va at about 220 Hz which is indicative of vibrational resonance. Trace Pa illustrates the phase lag between the excitation energy and the oscillations for the eye 1 having low IOP. At these low IOPs, the eye demonstrates more internal damping. Further, at low frequencies, it is believed that the whole eye is involved and at higher frequencies the response is more localized at the surface and demonstrates more phase lag.

Referring to FIG. 3b, trace Vb illustrates the velocity of an acoustically excited porcine's eye having a high IOP. Trace Pb illustrates the phase lag between the excitation energy and the oscillations of the eye. As anticipated, at higher IOP, the eye demonstrates higher stiffness which is beyond that inherent in the eye's mechanical properties alone, resulting in less lag in the phase of perturbing vibration and the measured vibration.

Returning to FIG. 4, note that resolution of the vibrational response is preferably increased using a higher driver force. Using acoustic energy, higher force is achieved by applying an acoustical wave at higher decibels. For better concentrating the acoustical energy onto the eye 1, and additionally for avoiding audio discomfort to a patient, there is provided a soft concave cup 22 for application over the eye 1. The back 23 of the cup 22 is fitted with a diaphragm 30 which is caused to oscillate resulting in a pressure wave to be impinged upon the eye 1. The cup 22 is pressed against the patient's forehead 26 and the cheek 27 to form a seal 25 over the eye. One or more transparent windows 24 are positioned in the back 23 of the cup 22 such that laser light 7,12 from the velocimeter and interferometer can pass therethrough and reflect off of the eye 1.

The combination of apparatus and methodology makes it possible to provide a portable IOP instrument which can be used by a patient at point-of-care rather than being limited to a clinical environment. A desktop or handheld unit incorporates a housing containing the means for a laser velocimeter, a laser interferometer, a non-contacting vibration source, a microprocessor and some form of IOP display—absolute or threshold. The housing incorporates locational means, such as a soft cup or nose rest for aligning the laser components for enabling reflection and measurement of the various reflected laser beams.

The embodiments of the invention for which an exclusive property or privilege is claimed is defined as follows:

1. A method of determining measures of intraocular pressure in an eye without contact with the eye comprising:
    applying a perturbing vibration to at least a portion of the eye without contact with the eye or eyelid for inducing an induced vibration in the surface of the eye;
    varying the frequency of the perturbing vibration;
    measuring a vibrational response of the induced vibration in the eye without contact with the eye or eyelid as the frequency of the perturbing vibration is varied for establishing characteristics indicative of mechanical properties of at least the portion of the eye including at least a stiffness property of the eye;
    measuring an axial length of the eye for establishing a volume of the eye; and
    determining measurements indicative of the intraocular pressure in the eye from the vibrational response, the mechanical properties and the volume of the eye.

2. The method as described in claim 1 wherein the vibrational response comprises a velocity of the induced vibration.

3. The method as described in claim 1 wherein the vibrational response comprises a phase lag between the perturbing vibration and the induced vibration.

4. The method as described in claim 1 wherein the vibrational response comprises a rate of change of a phase lag between the perturbing vibration and the induced vibration.

5. The method as described in claim 1 wherein the vibrational response comprises a velocity of the induced vibration and a comparison of the rate of change of a phase lag between the perturbing vibration and the induced vibration.

6. The method as described in claim 1 wherein the vibrational response is selected from the group of a velocity of the induced vibration, a magnitude of the velocity of the induced vibration, a phase lag between the perturbing vibration and the induced vibration, and a rate of change of the phase lag between the perturbing vibration and the induced vibration.

7. The method as described in claim 1 wherein the perturbing vibration is an acoustic wave.

8. The method as described in claim 5 wherein the vibrational response is measured using a laser velocimeter and laser doppler vibrometry techniques.

9. The method as described in claim 1 further comprising;
    providing a laser velocimeter producing a signal laser beam and a reference laser beam;
    directing the signal laser beam at the eye for forming at least one reflected laser beam; and
    combining the at least one reflected signal laser beam with a reference laser beam for creating interference indicative of the vibrational response.

10. The method as described in claim 9 wherein the vibrational response is at least a velocity of the induced vibration and a comparison of the rate of change of a phase lag between the signal laser beam and the at least one reflected laser beam.

11. The method as described in claim 9 wherein the vibrational response comprises one or more of: a velocity of the induced vibration, a magnitude of the velocity of the induced vibration, a phase lag between the perturbing vibration and the induced vibration, and a rate of change of the phase lag between the perturbing vibration and the induced vibration.

12. The method as described in claim 1 further comprising:
    providing a laser interferometer for producing a measuring beam directed at the eye and for producing interference patterns from a plurality of reflected beams reflected from the eye; and
    determining a path length between at least two of the plurality of reflected beams for establishing the axial length of the eye as a geometric characteristic related to the volume of the eye.

13. The method as described in claim 12 further comprising establishing a corneal thickness as a geometric characteristic of the eye by determining path lengths between at least two of the plurality of reflected beams.

14. The method as described in claim 1 further comprising:
    providing a laser velocimeter and a laser interferometer;
    applying the laser velocimeter to the eye for producing a reflected signal laser beam and combining the reflected signal laser beam with a reference laser beam for creating interference indicative of one or more vibrational responses;
    applying the laser interferometer for producing a measuring beam directed to the eye and receiving interference patterns from a plurality of reflected measurement beams reflected back from the vibrating eye and determining a path length between at least two of the reflected measurement beams for establishing the axial length of the eye as a geometric characteristic of the eye; and determining measurements indicative of the intraocular pressure in the eye from the vibrational response and the axial length of the eye.

15. The method as described in claim 14 wherein the mechanical properties of the eye comprise one or more of the stiffness of the eye and the water content of the cornea.

16. The method as described in claim 15 wherein the vibrational response comprises one or more of: a velocity of the induced vibration, a magnitude of the velocity of the induced vibration, a phase lag between the perturbing vibration and the induced vibration, and a rate of change of the phase lag between the perturbing vibration and the induced vibration.

17. The method as described in claim 14 wherein the vibrational response comprises one or more of: a velocity of the induced vibration, a magnitude of the velocity of the induced vibration, a phase lag between the perturbing vibration and the induced vibration, and a rate of change of the phase lag between the perturbing vibration and the induced vibration.

18. The method as described in claim 14 further comprising establishing a corneal thickness as a geometric characteristic of the eye by determining path lengths between at least two of the plurality of reflected beams.

* * * * *